US00PP15467P2

(12) United States Plant Patent
Olesen et al.

(10) Patent No.: US PP15,467 P2
(45) Date of Patent: Jan. 4, 2005

(54) HYBRID TEA ROSE VARIETY 'POULEN003'

(50) Latin Name: *Rosa hybrida*
Varietal Denomination: POULen003

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/341,892

(22) Filed: Jan. 13, 2003

(51) Int. Cl.[7] ..... A01H 5/00
(52) U.S. Cl. ..... Plt./137
(58) Field of Search ..... Plt./137

(56) References Cited

PUBLICATIONS

UPOV ROM GTITM Computer Database, GTI JOUVE Retrieval Software 2003/01 citation(s) for 'POULen003'.*
http://www.helpmefind.com/rose/pl.php?n=35704.*

* cited by examiner

*Primary Examiner*—Bruce R. Campell
*Assistant Examiner*—W C Haas

(57) ABSTRACT

A new garden rose plant which has abundant, light pink flowers and attractive foliage. This new and distinct variety has shown to be uniform and stable in the resulting generations from asexual propagation.

1 Drawing Sheet

Botanical classification: *Rosa hybrida.*
Variety denomination: 'POULen003'.

SUMMARY OF THE INVENTION

The present discovery constitutes a new and distinct variety of a Hybrid Tea rose plant which was discovered in a cultivated area. The mutation resulted from 'POULna', a Hybrid Tea rose hybridized by the same inventors. ('POULna') is described and illustrated in U.S. Plant patent application Ser. No. 09/268,566, dated Mar. 15, 1999, abandoned. The new rose variety resulted from a naturally occurring mutation of unknown causation on a branch of 'POULna'.

The new rose may be distinguished from 'POULna' by the following combination of characteristics:

1. While 'POULen003' has exhibits light pink blooms, 'POULna' exhibits creamy white colored blooms.
2. While 'POULen003' exhibits basal petal spots of Green-Yellow Group 1D, 'POULna' exhibits basal petal spots of Yellow-Green Group 144D.

The rose plant of the present discovery has a unique combination of characteristics which are outstanding in the new variety and which distinguish it from all other varieties which we are aware of.

For example, the new variety has:

1. Uniform and abundant light pink flowers;
2. Disease resistance;
3. Vigorous growth;
4. Exceptional fragrance.

This combination of qualities is not present in previously available commercial cultivars of this type and distinguish 'POULen003' from all other varieties of which we are aware.

The resulting mutation was selected and evaluations were conducted on the resulting rose plants in a controlled environment.

Asexual reproduction of 'POULen003' by cuttings was first done by L. Pernille and Mogens N. Olesen in Fredensborg, Denmark, in 1996. This initial and other subsequent propagations have demonstrated that the characteristics of 'POULen003' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULen003'. Specifically illustrated in the first drawing:

1. Stem showing branching and the attachment of leaves, buds, and peduncle;
2. Flower bud, partially opened bud, and open bloom;
3. Flower petals, detached.

DETAILED DESCRIPTION OF THE VARIETY

The following is a description of 'POULen003', as 3 year old budded plants, observed in its growth in a field nursery in Jackson County, Oreg. Color references are made using The Royal Horticultural Society (London, England) Colour Chart, 1995, except where common terms of color are used.

For a comparison, several physical characteristics of the rose variety 'POULheart', a rose variety from the same inventors described and illustrated in the U.S. Plant patent application Ser. No. 09/270,179 dated Mar. 15, 1999, now abandoned, is compared to 'POULen003' in Chart 1.

CHART 1

| | 'POULen003' | 'POULheart' |
|---|---|---|
| Petal color of outer petals after opening | White Group 155C with an overlay of Red Group 36D | White Group 155A |

CHART 1-continued

| | 'POULen003' | 'POULheart' |
|---|---|---|
| Petal count | 30 | 38 to 42 |
| Flower diameter when open | 60 to 70 mm | 90 to 120 mm |

Parents:
*Parent.*—'POULna'.
Classification:
*Botanical.*—*Rosa hybrida* 'POULen003'.
*Commercial.*—Hybrid Tea.

FLOWER AND FLOWER BUD

Blooming habit: Recurrent.
Flower bud:
*Size.*—Upon opening, 25 to 30 mm in length from base of receptacle to end of bud.
*Diameter.*—15 mm.
*Bud form.*—Very long pointed ovoid.
*Bud color.*—As sepals unfold, petals are White Group 155C; At ¼ opening, petals are White Group 155C.
*Sepals.*—Surfaces of sepals slightly pubescent. Stipitate glands are present along the margins and underside of the sepals. Color: Upper surface is Yellow Green Group 144D with intonations of Greyed-Red Group 181B. The lower surface is Green Group 143C. Shape: General sepal shape is ensiform to subulate. Sepal apex is cirrhose. Base is flat at union with receptacle. Margins: 2 of 5 sepals have margins which are entire. 3 of the 5 sepals have strong foliaceous apendages. Size: 30 mm long×8 to 10 mm wide. Receptacle: Surface: Smooth and glossy. Shape: Funnel shaped. Size: Small. 5 mm (h)×6 mm (w). Color: Yellow-Green Group 144B. Peduncle: Surface: Smooth with stipitate glands. Length: 50 to 60 mm average length. Diameter: 3.5 mm. Color: Yellow Green Group 144A and 144B. Strength: Somewhat strong. Borne: In small clusters with 3 to 5 buds per flowering stem.
*Anthocyanin.*—Greyed-Red 181C.
Flower bloom:
*Fragrance.*—Strong, traditional rose scent.
*Duration.*—The blooms have a duration on the plant of approximately 3 to 5 days. Petals fall cleanly away from plant.
*Size.*—Average flower diameter is 60 to 70 mm when open.
*Depth.*—40 mm.
*Form.*—Shape of flower when viewed from the side: Upon opening, upper part: Cupped. Upon opening, lower part: Convex. Open flower, upper part: Flat. Open flower, lower part: Convex.
*Petalage.*—Very double. Average range: 20 to 40 petals under normal conditions with no petaloids.
Color:
*Upon opening, petals.*—Outermost petals: Outer side: White Group 155C with an overlay of Red Group 36D. Inner Side: White Group 155C with an overlay of Red Group 36D. Innermost petals: Outer side: White Group 155C with an overlay of Red Group 36D. Inner Side: White Group 155C with an overlay of Red Group 36D.
*Upon opening, basal petal spots.*—Outermost petals: Outer side: Green-Yellow Group 1D. Inner Side: Green-Yellow Group 1D. Innermost petals: Outer side: Green-Yellow Group 1D. Inner Side: Green-Yellow Group 1D.
*After opening, petals.*—Outermost petals: Outer side: White Group 155C with overlay of Red Group 36D. Inner Side: White Group 155C with overlay of Red Group 36D. Innermost petals: Outer side: White Group 155C with overlay of Red Group 36D. Inner Side: White Group 155C with overlay of Red Group 36D.
*After opening, basal petal spots.*—Outermost petals: Outer side: Green-Yellow Group 1D. Inner Side: Green-Yellow Group 1D. Innermost petals: Outer side: Green-Yellow Group 1D. Inner Side: Green-Yellow Group 1D.
General tonality: On open flower very faint Red Group 36D. No change in the general tonality at the end of the 3rd day. Afterwards, general tonality is Red Group 36D.
Petals:
*Petal reflex.*—Strongly reflexed.
*Petal edge.*—Entire, with ruffles at margin.
*Shape.*—Deltoid shaped.
*Size.*—46 mm (l)×42 mm (w).
*Thickness.*—Average.
*Arrangement.*—Not formal.
Petaloids: None.
Reproductive organs:
*Pistils.*—Length: 15 mm long. Quantity: 38. Color: Overall coloration is White Group 155A with intonations of Red Group 47B underneath the stigma.
*Pollen.*—Color: None observed.
*Anthers.*—Size: 4 mm long. Color: Grey-Orange Group 163B. Quantity: 43.
*Filaments.*—Color: Green-Yellow Group 1D. Length: 12 mm.
*Stigmas.*—Inferior in location to anthers. Color: Greyed-Green Group 196C.
*Styles.*—Color: Green-Yellow Group 1D. Other intonations: Red Group 53D immediately below stigma.
*Hips.*—None observed.

PLANT

Plant growth: Vigorous, upright to bushy. As a budded field grown plant on *Rosa multiflora* understock, the average height of the plant itself is 100 to 150 cm and the average width is 100 cm.
Stems:
*Color.*—Young wood: Yellow-Green Group 144A. Older wood: Yellow-Green Group 144A.
*Size.*—90 cm length×10 mm diameter.
*Internodes distance.*—45 mm.
*Thorns.*—Incidence: 7 to 9 thorns per 10 cm of stem. Size: Average length: 10 mm. Color: Yellow-Green Group 144A with overlay of Greyed-Red Group 181C. Shape: Upper side is linear while the lower side is concave.
*Surface.*—Young wood: Smooth. Older wood: Rough.
Plant foliage: Normal number of leaflets on normal leaves in middle of the stem: 5 leaflets.
*Compound leaf size.*—120 mm (l)×95 mm (w).
*Quantity.*—Generally 3 leaves per 10 cm of stem on average.
*Color.*—Mature Foliage: Upper Leaf Surface: Green Group 137B. Lower Leaf Surface: Green Group 138B. Juvenile foliage: Upper Leaf Surface: Green Group 137B. Lower Leaf Surface: Green Group 138B. Anthocyanin intonation: Location: New growth of top leaves, rachis, petiole. Color: Greyed-Red Group 181C.

Plant leaves and leaflets:

*Stipules.*—Size: 5 mm wide by 20 mm long. Color: Yellow-Green Group 144A at margins. Yellow-Green Group 144C at mid rib of leaflet with intonations of Greyed-Red Group 181C. Margins: Stipitate Glands along the edges of the stipules. Anthocyanin: Greyed-Red Group 181C.

*Petiole.*—Length: 20 mm. Diameter: 3 mm. Color: Yellow-Green Group 144A. Underneath: Yellow-Green Group 144B. Margins: Stipitate glands observed on upper surface. Anthocyanin: Greyed-Red Group 181C.

*Rachis.*—Length: 55 mm. Color: Yellow-Green Group 144A. Margins: Stipitate glands present on upper surface. Anthocyanin: Greyed-Red Group 181C.

*Leaflet.*—Edge: Finely serrated. Size: 37 mm long by 32 mm wide. Shape: Broadly ovate. Apex is cuspidate. Base is round. Texture: Moderately glossy. Arrangement: Odd pinnate. Venation: Reticulate. Color: Yellow-Green Group 145A to Yellow-Green Group 151A.

Disease resistance: Average resistance to mildew, rust, black spot, and Botrytis under normal growing conditions in Jackson County, Oreg.

Cold hardiness: The variety 'POULen003' has been found to be cold tolerant to USDA Hardiness Zone 7 in Jackson County, Oreg.

It is claimed:

1. A new and distinct variety of rose plant of the Hybrid Tea class, substantially as herein illustrated and described as a distinct and novel rose variety due to its abundant light pink flowers, vigorous growth, disease resistance, and extended period of bloom.

* * * * *

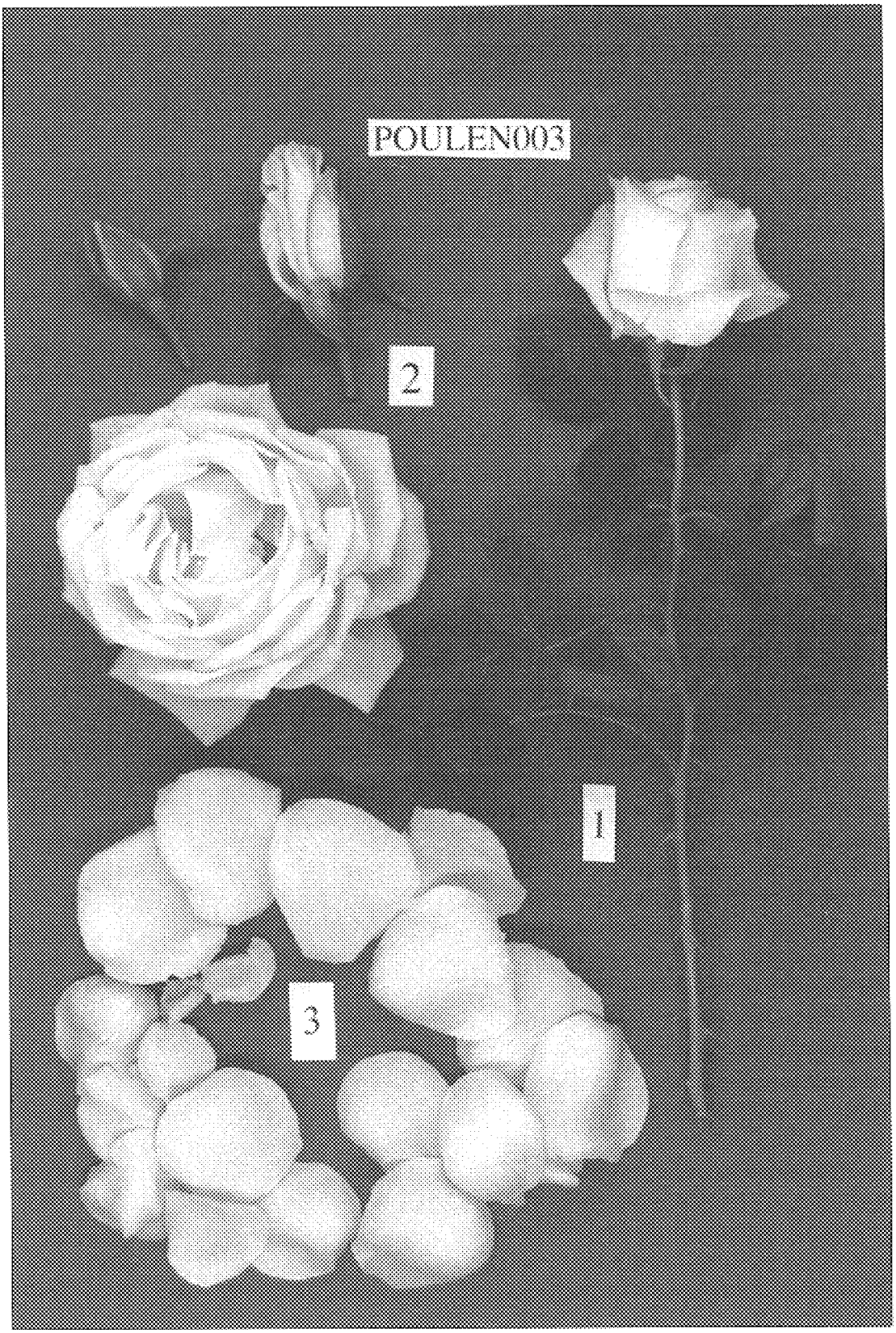
POULEN003
2
1
3